(12) United States Patent
Shuk et al.

(10) Patent No.: US 7,527,717 B2
(45) Date of Patent: May 5, 2009

(54) SULFUR RESISTANT SENSORS

(75) Inventors: Pavel Shuk, Copley, OH (US);
Ramasamy Manoharan, Wooster, OH (US); Tom Blanar, Wadsworth, OH (US); Ray Molnar, Twinsburg, OH (US); Marion Keyes, St. Louis, MO (US)

(73) Assignee: Rosemount Analytical, Inc., Orrville, OH (US)

( * ) Notice: Subject to any disclaimer, the term of this patent is extended or adjusted under 35 U.S.C. 154(b) by 715 days.

(21) Appl. No.: 10/607,856

(22) Filed: Jun. 27, 2003

(65) Prior Publication Data
US 2004/0134781 A1    Jul. 15, 2004

Related U.S. Application Data

(60) Provisional application No. 60/392,347, filed on Jun. 28, 2002.

(51) Int. Cl.
*G01N 27/409* (2006.01)
(52) U.S. Cl. .................. 204/424; 204/290.1; 204/427
(58) Field of Classification Search ......... 204/424–429, 204/431, 290.1; 205/784–785.5; 73/23.31; 422/94–97
See application file for complete search history.

(56) References Cited

U.S. PATENT DOCUMENTS

| | | | | |
|---|---|---|---|---|
| 2,916,358 A | * | 12/1959 | Glover et al. .................. 422/96 |
| 3,488,155 A | | 1/1970 | Auers | |
| 3,578,502 A | | 5/1971 | Tannenberger et al. ...... 136/120 |
| 3,687,631 A | * | 8/1972 | Zegel .......................... 436/152 |
| 3,759,087 A | * | 9/1973 | Iwao et al. ............... 73/863.12 |
| 3,785,948 A | | 1/1974 | Hitchman et al. | |
| 3,897,267 A | * | 7/1975 | Tseung et al. ................ 607/35 |
| RE28,792 E | | 4/1976 | Ruka et al. .................... 204/1 |
| 3,981,785 A | | 9/1976 | Sandler | |
| 4,101,404 A | * | 7/1978 | Blumenthal et al. ......... 204/428 |
| 4,134,818 A | | 1/1979 | Pebler et al. | |
| 4,135,382 A | | 1/1979 | Capone ........................ 73/23 |
| 4,141,955 A | | 2/1979 | Obiaya | |
| 4,186,072 A | | 1/1980 | Blumenthal et al. ......... 204/195 |
| 4,355,056 A | * | 10/1982 | Dalla Betta et al. ...... 427/126.4 |

(Continued)

FOREIGN PATENT DOCUMENTS

EP    0 485 085    5/1992

(Continued)

OTHER PUBLICATIONS

Certified translation of JP 11-271269 A by Inaba et al, Oct. 1999.*

(Continued)

*Primary Examiner*—Kaj K Olsen
(74) *Attorney, Agent, or Firm*—Christopher R. Christenson; Westman, Champlin & Kelly, P.A.

(57) ABSTRACT

Sulfur resistant sensors and a process analytic system employing such sensors are provided. The sensors generally include a treatment or material that is adapted to increase the resistance of certain portions of the sensors to exposure to sulfur. In one aspect, an improved sulfur-resistant process analytic system includes a probe with one or more sulfur-resistant sensors therein coupled to a controller, a thermal control module, and a source of blowback gas.

6 Claims, 20 Drawing Sheets

U.S. PATENT DOCUMENTS

| | | | | |
|---|---|---|---|---|
| 4,428,817 A | * | 1/1984 | Isenberg | 204/412 |
| 4,618,855 A | | 10/1986 | Harding et al. | 340/605 |
| 4,702,971 A | | 10/1987 | Isenberg | 429/31 |
| 4,977,385 A | * | 12/1990 | McQueen | 338/24 |
| 4,994,780 A | * | 2/1991 | McQueen | 338/24 |
| 5,021,304 A | * | 6/1991 | Ruka et al. | 429/30 |
| 5,106,654 A | * | 4/1992 | Isenberg | 427/115 |
| 5,314,828 A | * | 5/1994 | Dalla Betta et al. | 436/118 |
| 5,338,515 A | * | 8/1994 | Dalla Betta et al. | 422/95 |
| 5,444,974 A | * | 8/1995 | Beck et al. | 60/274 |
| 5,627,328 A | * | 5/1997 | Sheridan et al. | 73/863.83 |
| 5,676,811 A | * | 10/1997 | Makino et al. | 204/425 |
| 5,695,624 A | | 12/1997 | Garzon et al. | 204/425 |
| 5,766,789 A | * | 6/1998 | James et al. | 429/44 |
| 5,827,415 A | | 10/1998 | Gur et al. | 204/426 |
| 6,009,742 A | | 1/2000 | Balko | 73/23.31 |
| 6,110,861 A | * | 8/2000 | Krumpelt et al. | 502/326 |
| 6,368,479 B1 | * | 4/2002 | Yokota et al. | 204/424 |
| 6,521,202 B1 | * | 2/2003 | Vaughey et al. | 423/599 |
| 2002/0172633 A1 | | 11/2002 | Koermer et al. | 423/219 |

FOREIGN PATENT DOCUMENTS

| | | |
|---|---|---|
| EP | 0 608 122 | 7/1994 |
| GB | 756662 | 9/1956 |
| GB | 761055 | 11/1956 |
| GB | 2 104 666 A * | 3/1983 |
| JP | 08220060 | 8/1996 |
| JP | 10090127 | 4/1998 |
| WO | WO 91/19975 | 12/1991 |

OTHER PUBLICATIONS

Garzon, Fernando, et al., "Solid-State Mixed Potential Gas Sensors: Theory, Experiments and Challenges," Solid State Ionics, North Holland Publication Company, Amsterdam, NL, vol. 136-137, Nov. 2, 2000, pp. 633-638.

Mukundan, R., et al., "Ceria-Electrolyte-Based Mixed Potential Sensors for the Detection of Hydrocarbons and Carbon Monoxide," Electrochemical and Solid-State Letters, IEEE Service Center, Piscataway, NJ, Aug. 1999, pp. 412-414.

Brosha, Eric, et al., "Mixed Potential Sensors Using Lanthanum Manganate and Terbium Yttrium Zirconium Oxide Electrodes," Sensors and Actuators, Elsevier Sequoia, vol. 87, No. 1, Nov. 15, 2002, pp. 47-57.

"Xendos 2700," Servomex, www.analyzer.com/Brochures/Servomex/2700tds.pdf.

The Examination Report for Application No. 03762135.6, filed Jun. 27, 2003.

Miura et al., "Progress in Mixed-Potential Type Devices Based on Solid Electrolyte For Sensing Redox Gases," Solid States Ionics, pp. 533-542, 2000.

Miura et al., "Highly Selective CO Sensor Using Stabilized Zirconia and a Couple of Oxide Electrodes," Sensors and Actuators, pp. 84-91, 1998.

Oto et al., "New Semiconductor Type Gas Sensor for Air Quality Control in Automobile Cabin," Sensors and Actuators, pp. 525-528, 2001.

Garzon et al., "Solid-State Mixed Potential Gas Sensors: Theory, Experiments and Challenges," Solid State Ionics, pp. 633-638, 2000.

Brailsford et al., "A First Principles Model of Metal Oxide Gas Sensors for Measuring Combustibles," Sensors and Actuators, pp. 93-100, 1998.

Seiyama, T. et al., "A New Detector for Gaseous Component Using Semiconductive Gas Sensors," Anal Chem, vol. 34, 1962, p. 1502.

Heiland, G., et al., "Physical and Chemical Aspects of Oxidic Semiconductor Gas Sensors," Chemical Sensor Technology, vol. 1, 1988, pp. 15-38.

Fleming, W., "Physical Principles Governing Nonideal Behavior of the Zirconia Oxygen Sensor," Journal of the Electrochemical Society, vol. 124, 1977, pp. 21-28.

Shimizu, F. et al., Chemistry Letters, Chemical Society of Japan, 1972.

Okamoto, H., "Carbon Monoxide Gas Sensor Made of Stabilized Zirconia," Solid State Ionics, vol. 1, pp. 319-326.

Garzon, Fernando, et al., "Solid-State Mixed Potential Gas Sensors: Theory, Experiments and Challenges," Solid State Ionics, North Holland Publication Company, Amsterdam, NL, vol. 136-137, Nov. 2, 2000, pp. 633-638.

"Xendos 2700," Servomex, www.analyzer.com/Brochures/Servomex/2700tds.pdf, date unknown.

P. Shuk, M. Greenblatt, Hydrothermal Synthesis and Properties of Mixed Conductors Based On $Ce_{1-x}Pr_xO_{2-x/2}$ Solid Solutions. Solid State Ionics. 116 (1999)217.

P. Shuk, M. Greenblatt, and M. Croft, Hydrothermal Synthesis and Properties of the Mixed Conducting $Ce_{1-x}Tb_xO_{2-x/2}$ Solid Solutions. Chem. Mater. 11 (1999)473.

Search Report from European Patent Office for foreign application PCT/US03/20327, filed Jun. 27, 2003.

Kirchnerova, J., "Materials for Catalytic Gas Combustion," Korean J. Chem. Eng., 16(4), pp. 427-433 (1990).

Summons to Attend Oral Proceedings for European patent application 03762135.6, dated Feb. 23, 2009.

* cited by examiner

SULFUR RESISTANT SENSORS

CROSS-REFERENCE TO RELATED APPLICATIONS

The present application is based on and claims the benefit of U.S. provisional patent application Ser. No. 60/392,347, filed Jun. 28, 2002, entitled Sulfur Resistant Sensors, the content of which is hereby incorporated by reference in its entirety.

BACKGROUND OF THE INVENTION

Process analytic systems are used in a variety of industries to sense the quantity and/or quality of one or more analytical parameters of interest. One example of such an environment is the combustion process itself. Combustion generally consumes a quantity of oxygen and an organic compound and provides, ideally, carbon dioxide and water. In the real world, however, combustion is often not totally complete. This leaves a relatively small quantity of unused non-combusted material referred to hereinafter as "combustibles" and/or unused oxygen. There are certainly other environments in which knowledge of the concentration of combustibles and/or oxygen is desirable, and aspects of the present invention described herein are usable in such environments as well.

Many process analytic sensors use platinum and/or compounds thereof for sensing. Platinum provides a number of advantages in that it is generally highly robust in most analytic environments and provides temperature sensitivity. Temperature sensitivity means that generally, as the temperature of platinum metal changes, the resistance thereof will change in a predictable manner. Accordingly platinum is a frequently used and effective material in high temperature process analytic environments, and is widely used in both combustible sensors and oxygen sensors.

One potential drawback of platinum as a component of such sensors arises when sulfur-containing compounds are exposed to the sensor. Under reducing conditions, sulfur dioxide, for example, will react with combustibles present in a flue stream thereby forming gaseous sulfur in the following manner.

$$SO_2 + 2CO \leftrightarrows S(g) + 2CO_2$$

Gaseous sulfur subsequently reacts with platinum materials within the sensor forming volatile mixed valence platinum sulfides as described by G. Zwingmann and E. M. Wenzel, Reaction of Sulfur and Sulfur Containing Substances With Pt, Rd and Pt/Rd Alloys, METALL. 25 (1971) 1121. The reaction with sulfur can lead to evaporation of platinum within the sensor especially when it is disposed on ceramic such as in the case of analytic oxygen sensors and can lead to rapid electrode deterioration within the sensors.

With respect to prior art sensor electrodes, sulfur tolerance of composite electrodes has been taught. For example, U.S. Pat. No. 4,702,971 teaches a sulfur tolerant composite cermet electrode for solid oxide electrochemical cells. These electrodes can include an oxide selected from the group zirconium, yttrium, scandium, thorium, rare earth metals, and mixtures thereof. More reliable mixed conducting materials have been developed based on fluorite-type oxide ion conducting solid electrolytes, i.e. based on ceria, having considerably higher ionic and electronic conductivity. A description of such materials can be found in a paper by P. Shuk, M. Greenblatt and M. Croft, entitled "Hydrothermal Synthesis and Properties of the Mixed Conducting $Ce_{1-x}Tb_xO_{2-x/2}$ Solid Solutions. CHEM. MATER. 11 (1999) 473.

Providing process analytic electrochemical sensors that can withstand the high temperature environments of today's industrial demands while simultaneously resisting the effects of sulfur in sulfur-containing environments would be a vast improvement to the art since sulfur is present, to a greater or lesser degree in many environments. Additionally, analytical sensors which last longer in such environments necessarily reduce the amount of technician time required to maintain the process and may even potentially reduce overall operation cost of the combustion operation.

SUMMARY OF THE INVENTION

Sulfur resistant sensors and a process analytic system employing such sensors are provided. Specifically three types of sensors are provided: calorimetric, potentiometric and mixed potential type potentiometric for combustible gas and oxygen. The sensors generally include a treatment or material that is adapted to increase the resistance of certain portions of the sensors to exposure to sulfur. In one aspect, an improved sulfur-resistant process analytic system includes a probe with one or more sulfur-resistant sensors therein coupled to a controller, a thermal control module, and a source of blowback gas.

DETAILED DESCRIPTION OF THE PREFERRED EMBODIMENTS

Embodiments of the present invention will be described with respect to specific types of electrochemical sensors and their particular adaptation for operation within sulfur containing environments. However, the invention is not limited to the embodiments described.

Sulfur Resistive Combustible Electrochemical Sensor

Combustible sensors typically include an oxide ion-conducting solid electrolyte and two or more electrodes with different catalytic activity to combustion reactions. All electrodes are exposed to a combustion exhaust stream and the sensor signal/potential between an inactive electrode (reference) and a catalytically active electrode (working) for a given specie is proportional to specie concentration.

One example of such combustible sensors is known is as a potentiometric solid electrolyte sensor. The zirconia based electrochemical oxygen sensors are typically used as a basis for measuring oxygen partial pressure in various combustion processes. These sensors can form the basis of an improved combustibles sensor as will be described below. The oxygen sensor will typically consist of two porous platinum electrodes deposited on opposite sides of a tube or disc-shaped zirconia electrolyte. The response of the sensor to the differential in oxygen partial pressure on the reference (exposed to the gas mixture with known oxygen partial pressure, e.g. air) and the process side (exposed to the analyzed gas) obeys the Nernst type equation of the following form.

$$EMF = \frac{RT}{4F} \ln \frac{P_{meas}}{P_{ref}} + C$$
$$= S \log \frac{P_{meas}}{P_{ref}} + C$$
$$= 0.0496 * T * \log \frac{P_{meas}}{P_{ref}} + C,$$

where EMF is the measured electromotive force (is negative potential), R is the gas constant, T is the absolute temperature, F is the Faraday constant and $S=RT/4F=0.0496*T$ is the cell slope, C is the cell constant, including different thermal and cell design effects.

When the electrodes within the sensor are exposed to the same gas atmosphere, the potential of the sensor will equal C and will be constant at fixed temperature if the electrode activities are equal. Using electrodes of different activities to the combustion reaction, allows a sensor to be designed for sensitivity to specific gas species. Platinum has traditionally been used for the sensors since platinum is a known catalytically active material. However, as described above, the presence of platinum in a sulfur containing flue exhaust stream can be susceptible to working electrode degradation in premature sensor failure.

Figure 1:
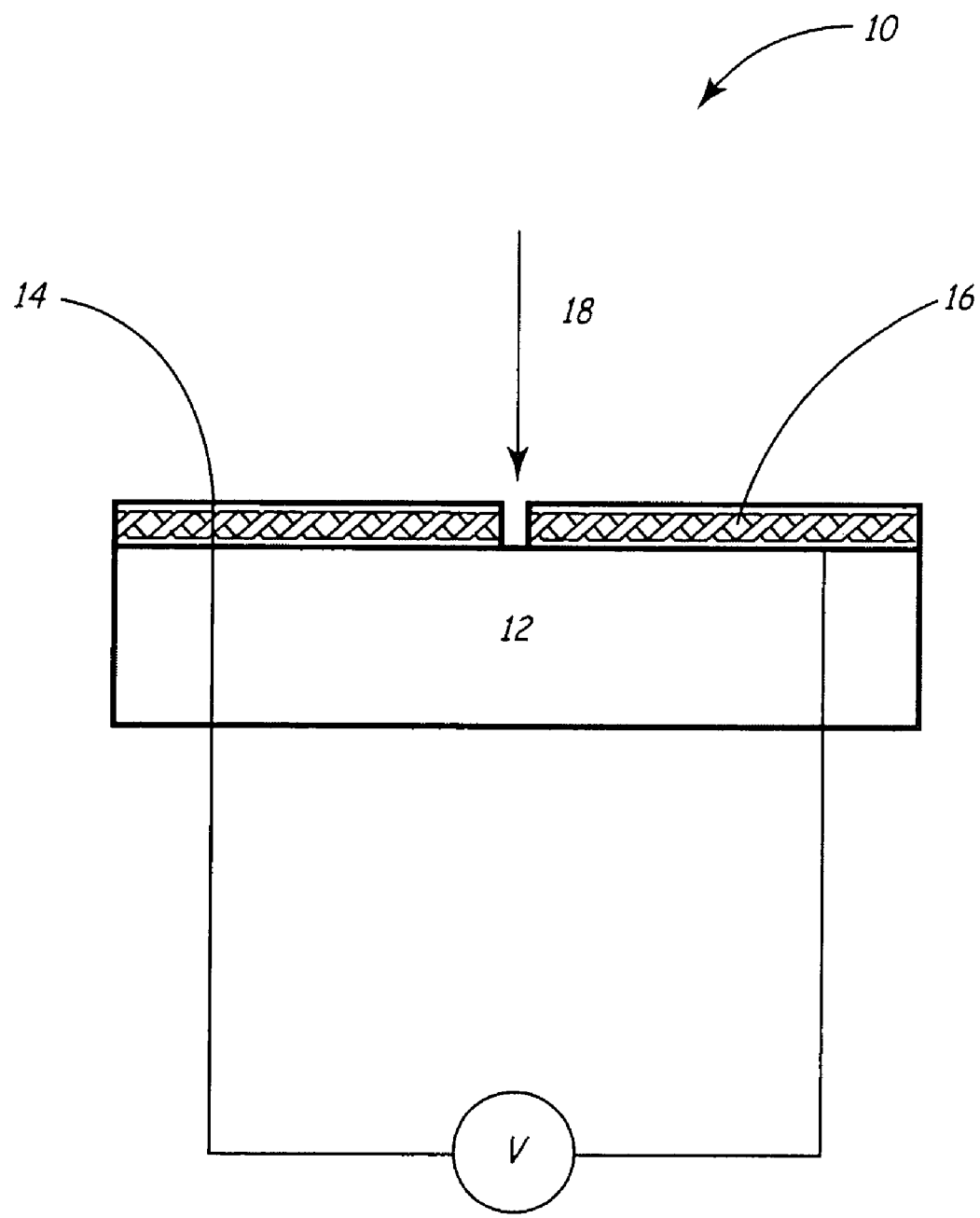
FIG. 1 is a diagrammatic view of a combustible sensor in accordance with embodiment of the present invention.

FIG. 1 is a diagrammatic view of a combustible sensor in accordance with embodiments of the present invention.

Sensor 10 includes an oxygen ion-conducting solid electrolyte disc/plate indicated at 12 upon which are disposed reference electrode 14 and working electrode or process electrode 16. Electrolyte 12 is preferably doped zirconia, ceria, or bismuth oxide. As illustrated in FIG. 1, electrodes 14 and 16 are disposed on the same surface of the disc/plate 12. Reference electrode 14 is preferably constructed from material selected from the noble metal or oxide group, preferably gold (Au) with no catalytic action to the combustion reaction. Additionally, electrode 14 can be constructed from doped lanthanoide chromite. Process electrode 16 is preferably constructed from a material that is a catalyst to the combustion reaction and is exposed to the analyzed gas stream. Preferably, electrode 16 can be constructed from platinum or other electron/mixed conducting metals or metal oxide electrodes. More preferably, electrode 16 is constructed from a material selected from the fluorite or perovskite group of materials, and even more preferably is calcium or magnesium substituted lanthanum manganite or mixed conducting ceria.

Figure 2:
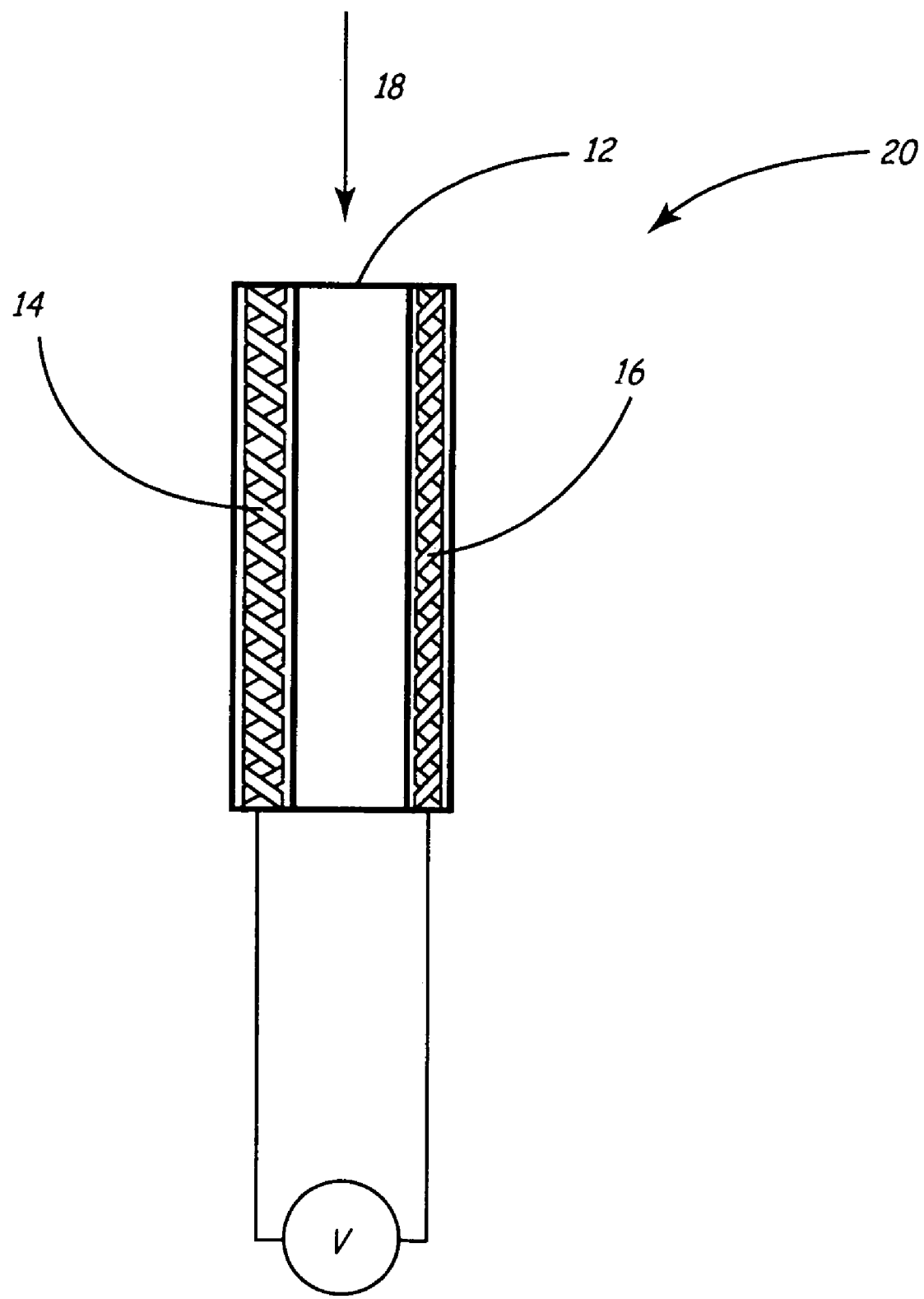
FIG. 2 is a diagrammatic view of a combustible sensor in accordance with an alternate embodiment of the present invention.

FIG. 2 is a diagrammatic view of an electrochemical combustible sensor in accordance with an alternate embodiment of the present invention. Sensor 20 includes disc 12, and electrodes 14 and 16 disposed on opposite sides of disc 12. In both FIGS. 1 and 2, flue gas is exposed as indicated at arrow 18.

A sensor constructed in accordance with the description above can produce a thermal-EMF related to different temperature of the electrodes based on the concentration of combustibles exposed to the working electrode. The heat release in the combustion reaction on the working/active electrode will increase the temperature of that electrode relative to the reference electrode and a thermal-EMF of 10-200 millivolts, depending on the combustion species concentration will be produced.

Figure 3:
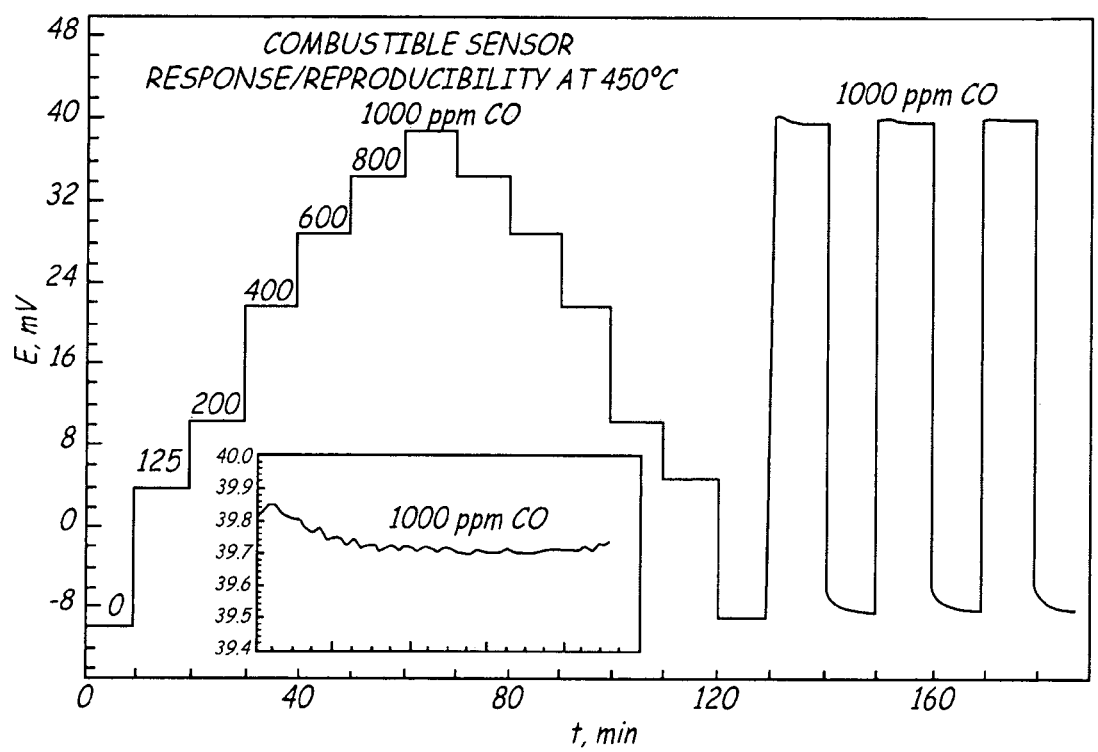
FIGS. 3-6 are charts illustrating combustible sensor response, calibration and material stability.
Figure 4:
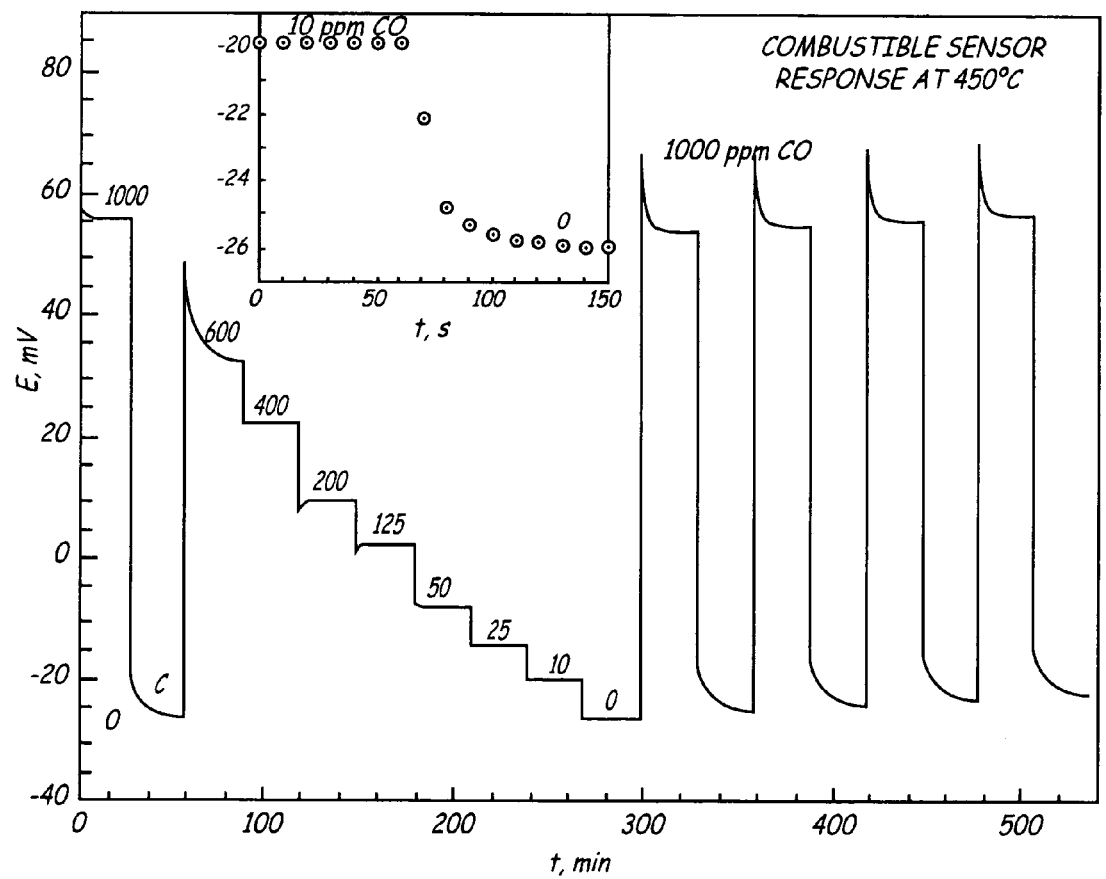
Figure 5:
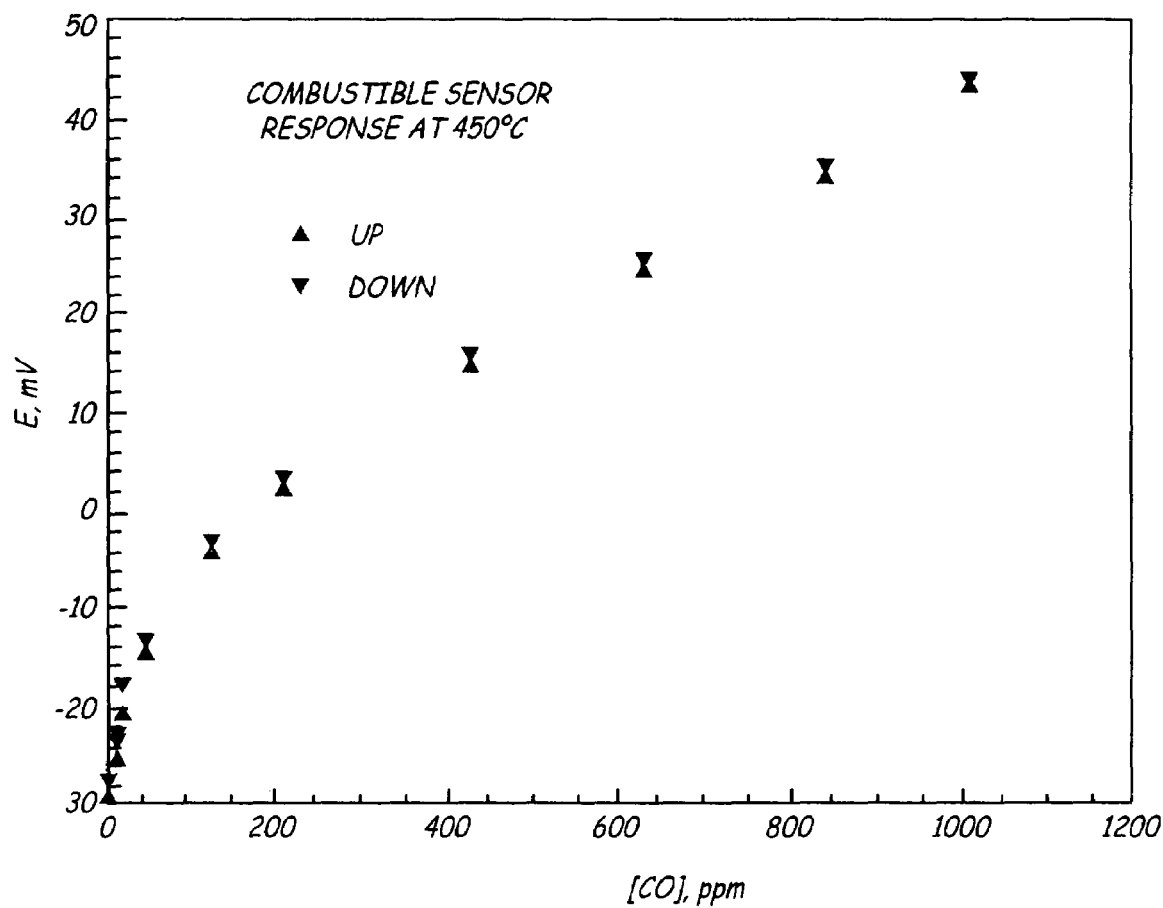
Figure 6:
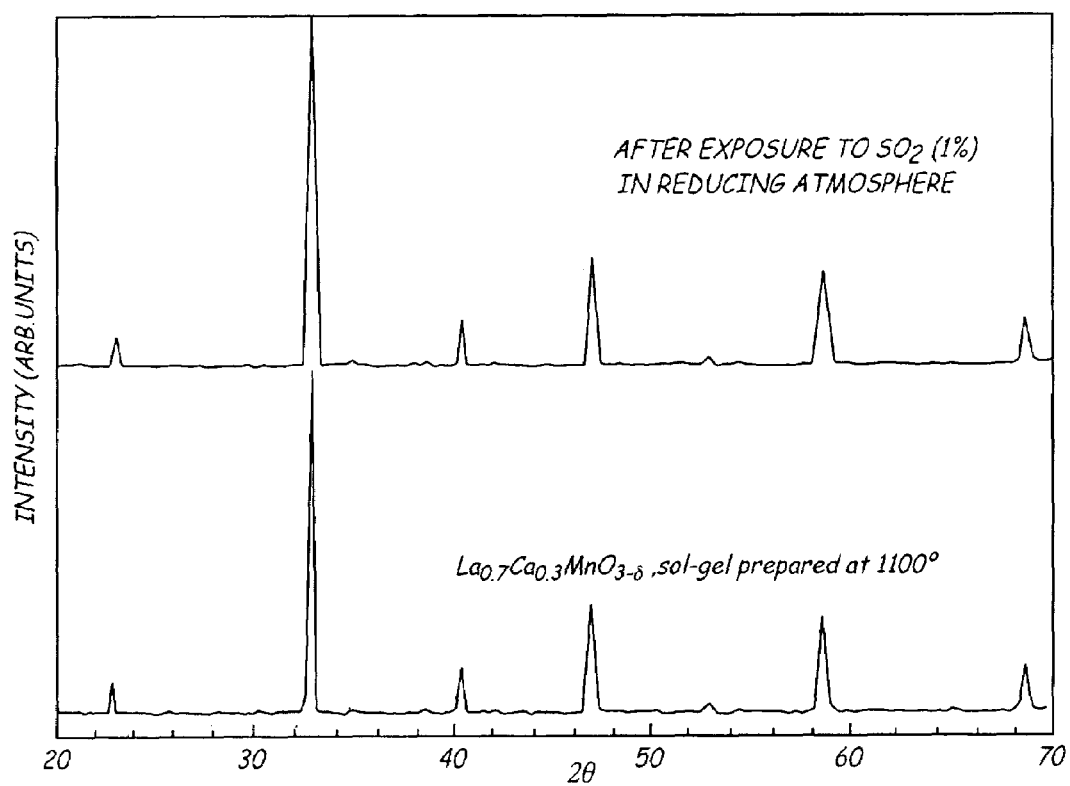

Combustible electrochemical sensors as described herein exhibit relatively high and reproducible sensitivity to carbon monoxide in a relatively wide range of carbon monoxide concentrations. This behavior is illustrated in FIGS. 3 and 4 which provide charts of combustible sensor response to varying levels of carbon monoxide. FIG. 5 illustrates an added benefit of an embodiment of the present invention. Specifically, electrochemical combustible sensors in accordance with embodiments of the present invention exhibit desirable sensitivity at lower carbon monoxide concentrations, particularly in the range of 5-50 parts per million. Adjusting the specific area of the working electrode provides the sensor with a high sensitivity to different carbon monoxide ranges, as desired. The sensor materials, e.g. zirconia and gold, are also known to be stable in high sulfur environments. The tests of manganite process electrode indicate that any change in the structure after exposure to sulfur dioxide at 1,000° C. for two weeks (FIG. 6) is both stable and reproducible in response to carbon monoxide in high sulfur environments, as opposed to platinum-containing combustible sensors.

Sulfur Resistive RTD Type Combustible Sensor

Another form of combustible sensor is that based on resistance temperature devices (RTD). In accordance with one embodiment of the present invention, an improved combustible sensor includes two RTDs covered by a metal (preferably stainless steel or Inconel) one-ended closed protector tubes, one with catalyst (such as platinum) and another with or without a reference film. The reference and the catalyst RTD's are exposed to the exhaust stream and the sensor signal is based upon the resistance difference between the reference and catalyst RTD for the given specie. The difference in resistance between the reference and catalyst RTD due to the heat released in combustion reaction on catalyst RTD is proportional to the specie concentration. The sensor is designed to be stable in sulfur containing atmospheres and is accordingly not sensitive to oxides of sulfur.

In the past, combustible sensors have employed the concept of comparing the temperature differential developed between a reference junction and a catalyst junction using thermocouples or thermopiles. For example, see U.S. Pat. No. 4,141,955, which discloses a combustible concentration analyzer. However, more sensitive combustible sensors can be built, in accordance with embodiments of the present invention using appropriate catalysts for the combustion reaction maintained in direct contact with the protective cover of the RTDs as well as an optional reference RTD for temperature control. The difference between the two reference and catalyst RTD signals, will then be directly correlated to the combustible concentration.

The concept of using temperature change of a gas as it passes through a catalyst bed as an indicator of content of a gas mixture is known. For example, U.S. Pat. No. 3,488,155 teaches using a temperature difference on a hydrogenation catalyst bed that can be related to hydrogen content of an incoming gas stream. U.S. Pat. No. 5,314,828 suggests using a $NO_x$ sensor and process for detecting $NO_x$ using a suitable catalyst and different temperature measuring devices (i.e. thermocouples and RTDs). However, none of these materials actually suggest using a process or apparatus in which a catalyst sensor element is actually used to detect combustibles, nor teach the functionally specific configuration of an RTD system and catalyst film sensor elements. Further, none of the disclosures listed above, nor in the prior art, suggest using such a sensor in a sulfur containing atmosphere and ensuring that such sensor is not sensitive to $SO_2$.

Some embodiments of the present invention provide a combustible sensor, and more particularly, an RTD-type sensor. Preferably, the RTD sensing element used in accordance with embodiments of the present invention consists of a wire coil or deposited film of pure metal that has a resistance that increases with temperature in a known and repeatable manner.

Figure 7:
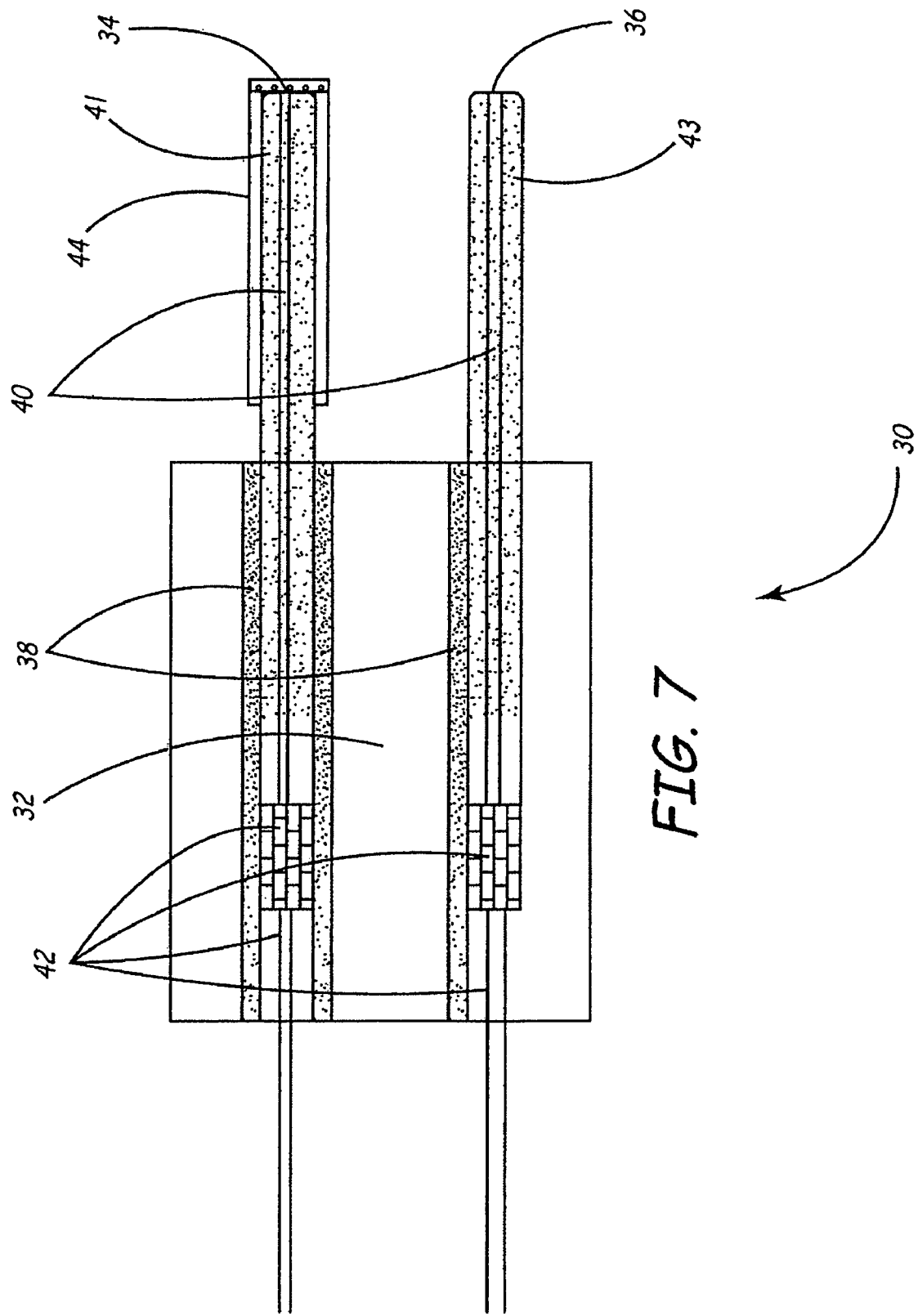
FIG. 7 is a diagrammatic view of an RTD-type combustible sensor in accordance with embodiment of the present invention.
Figure 8:
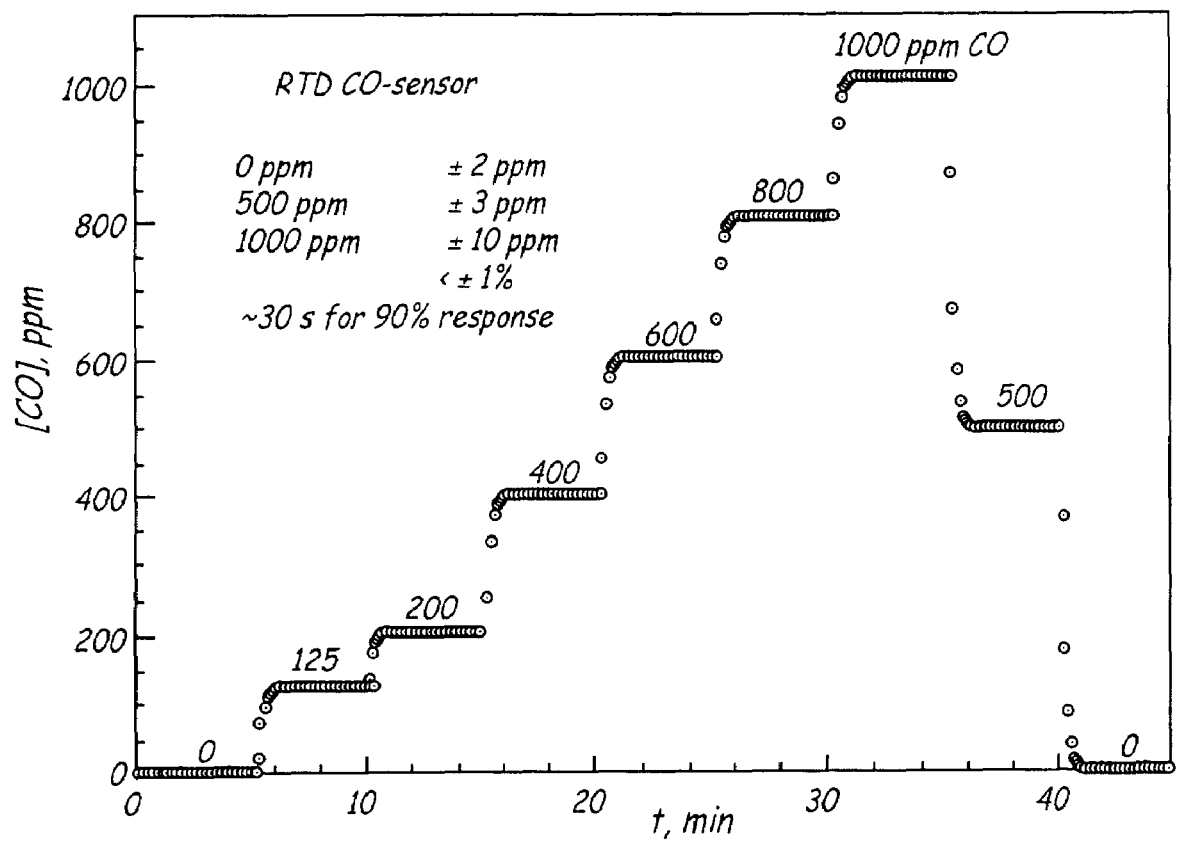
FIGS. 8-14 are charts of sensor response, stability, stability, cross sensitivity and field beta test.
Figure 9:
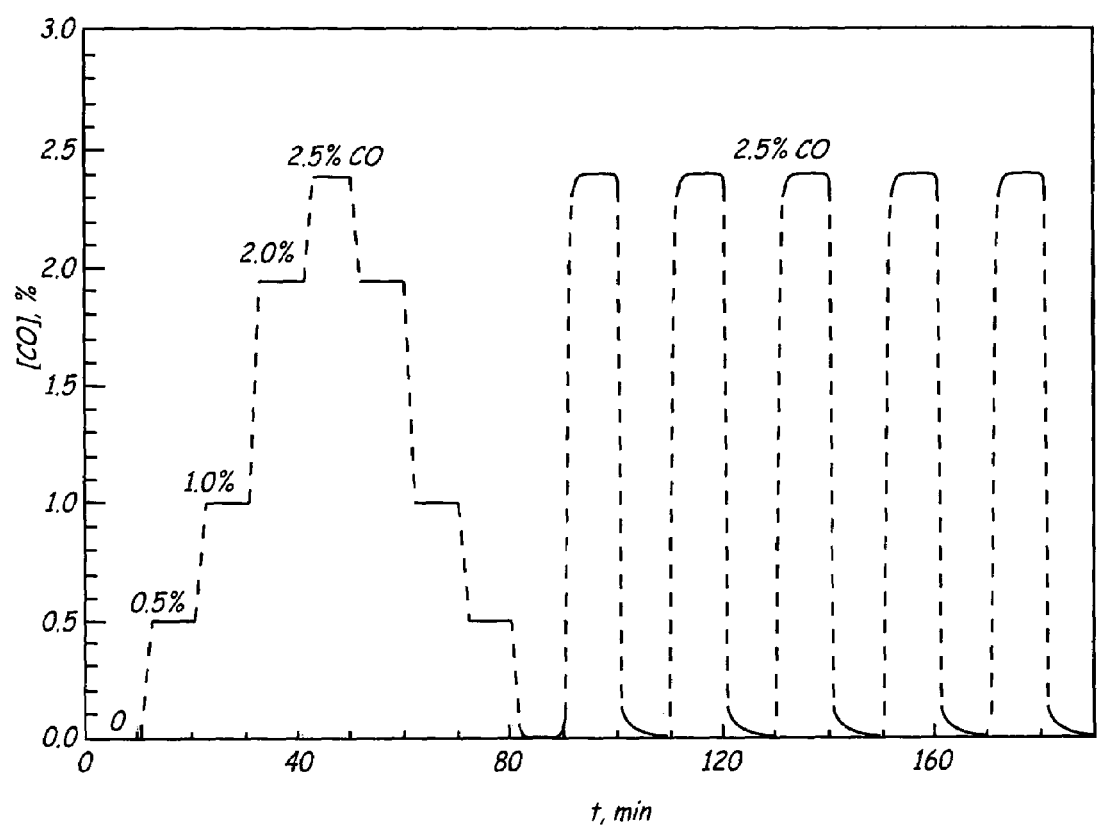
Figure 10:
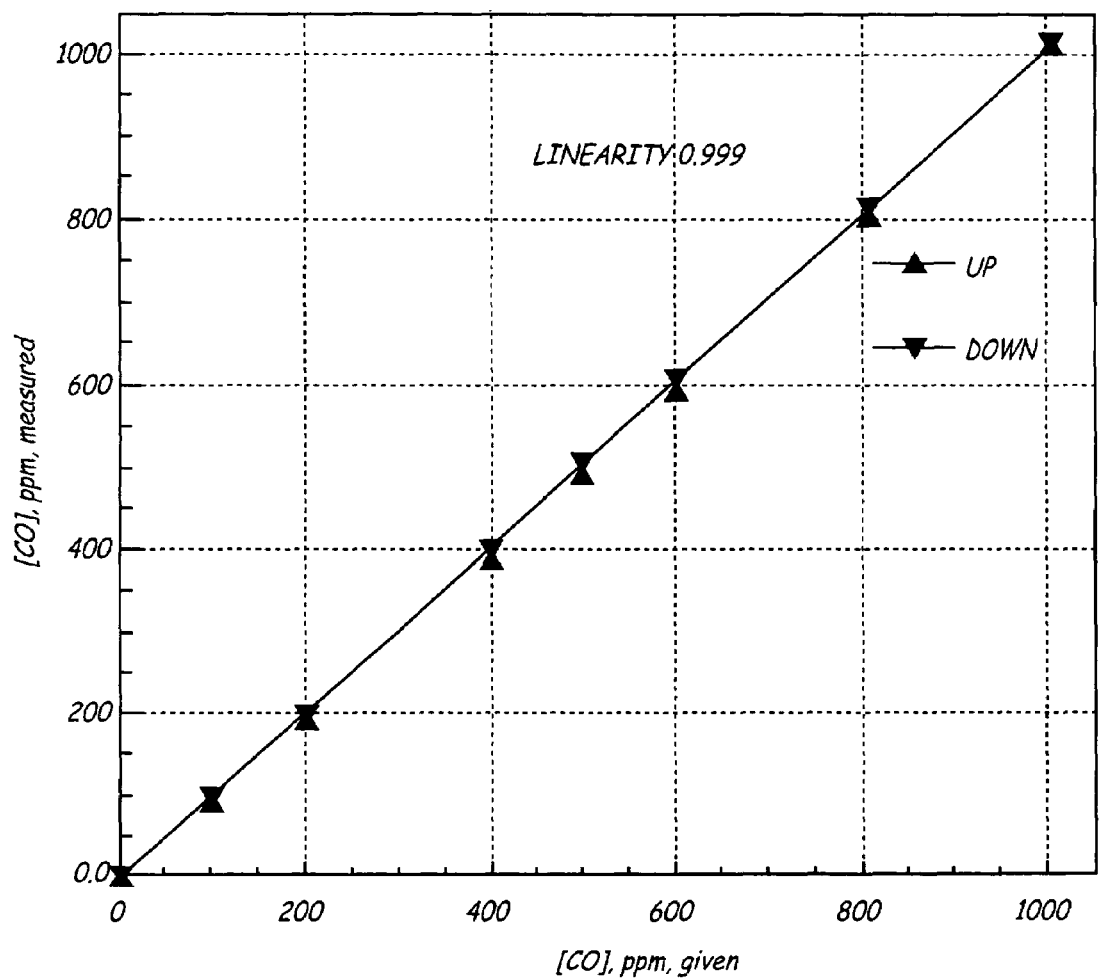
Figure 11:
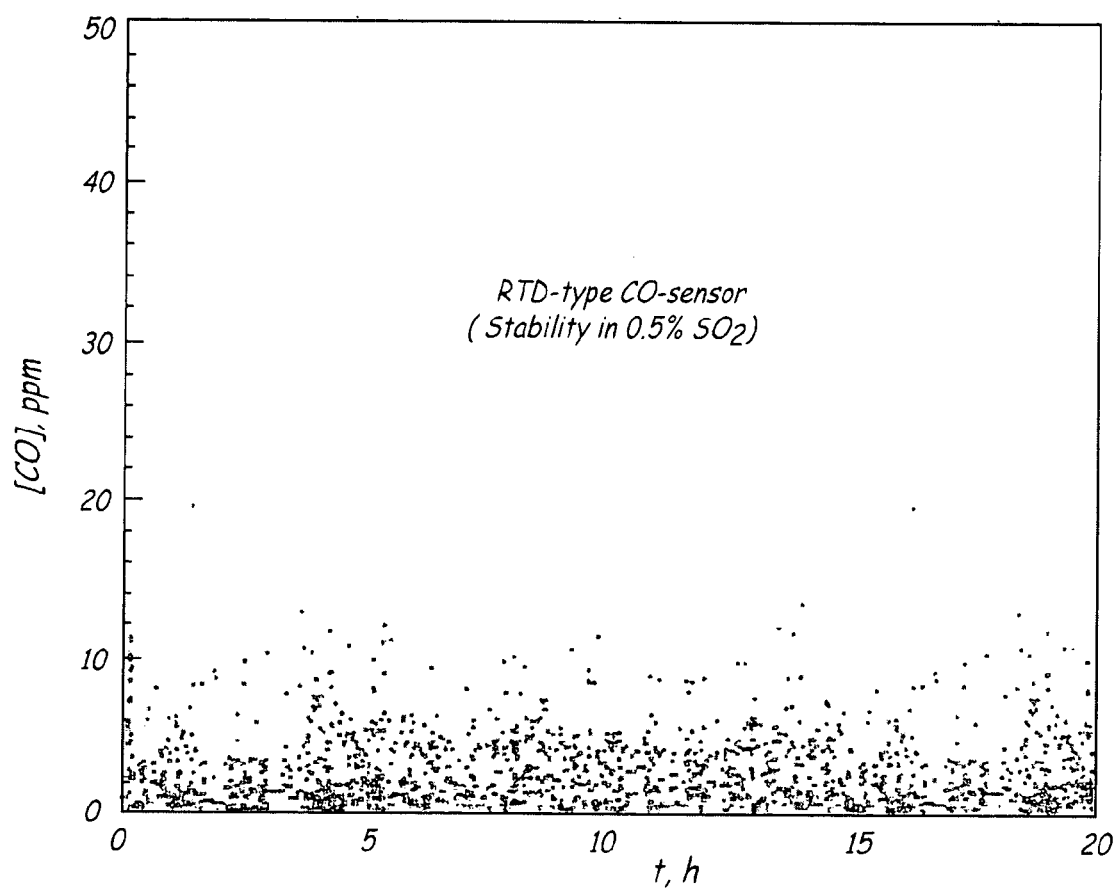
Figure 12:
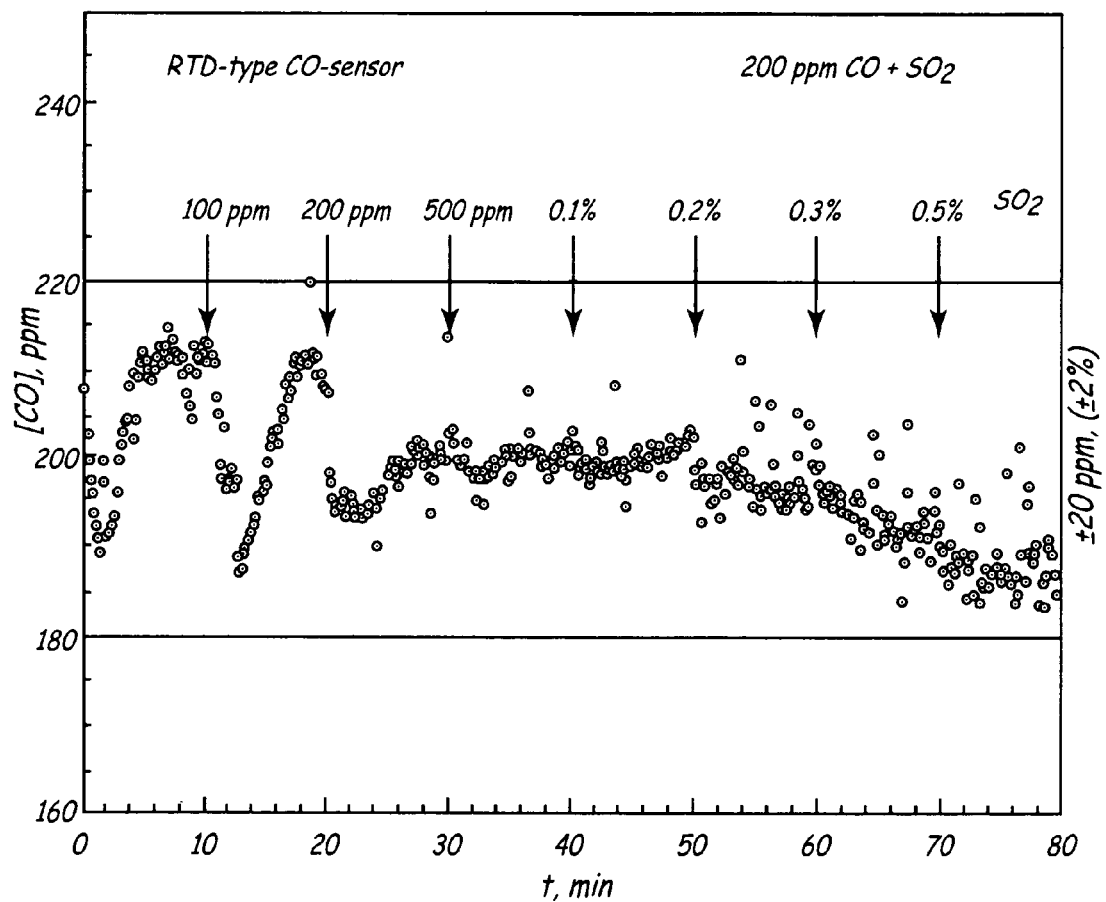
Figure 13:
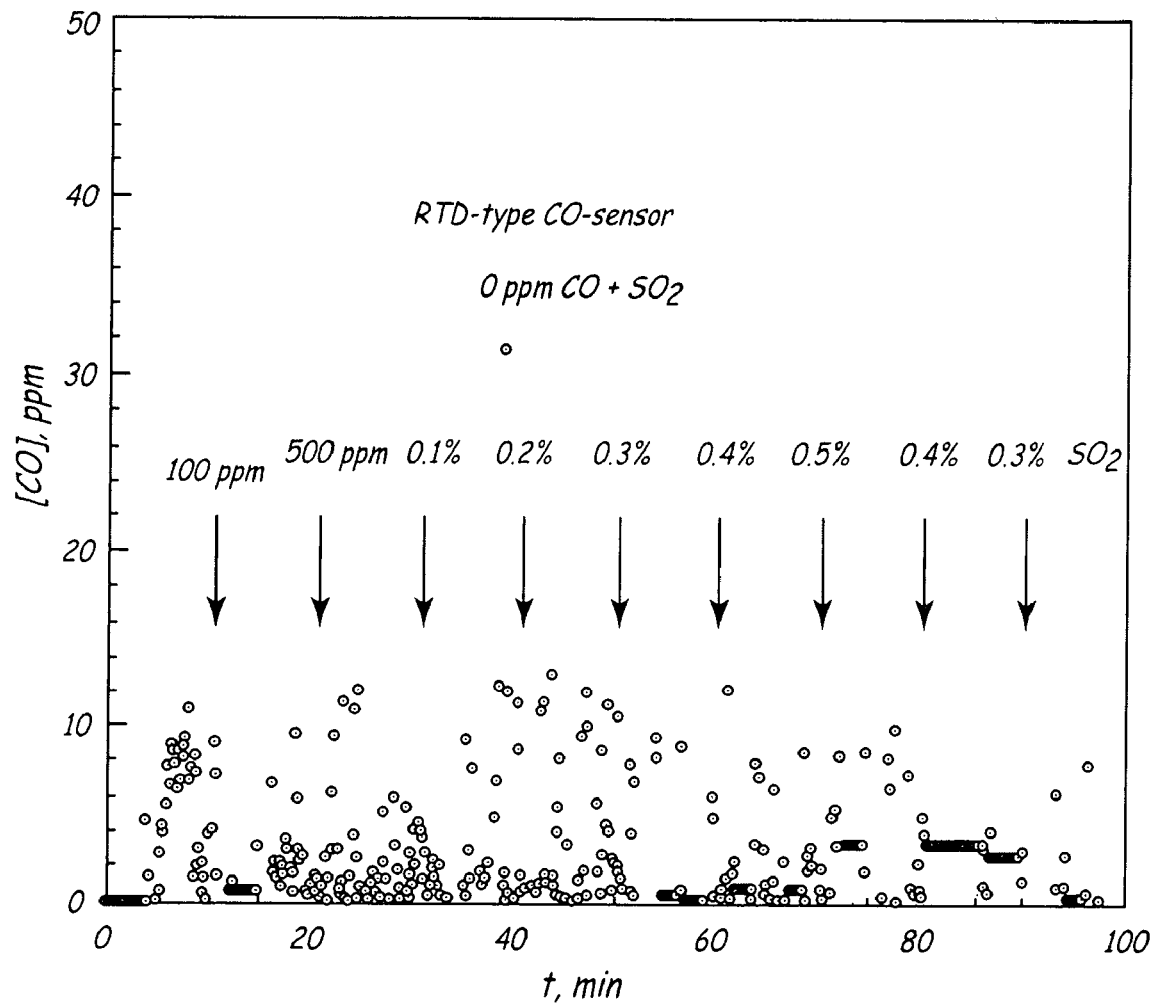
Figure 14:
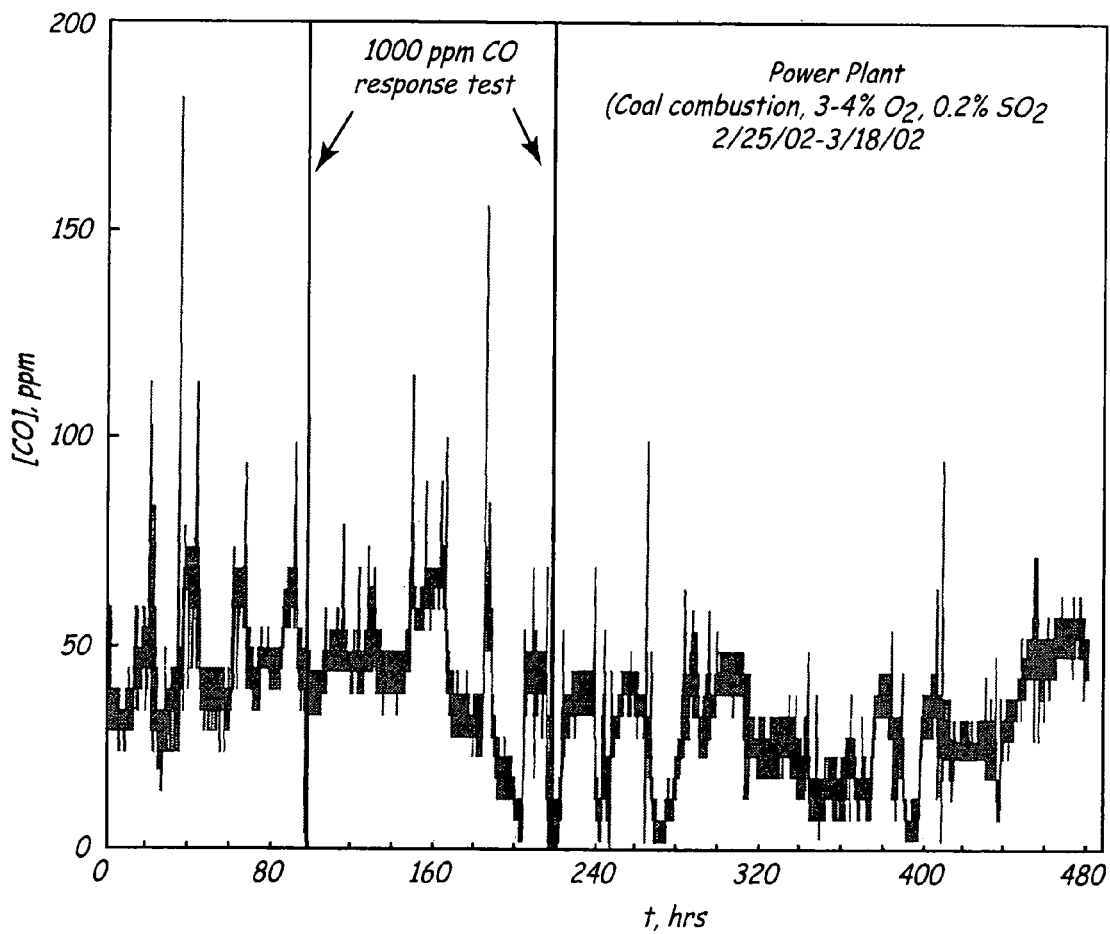

FIG. 7 is a diagrammatic view of a RTD-type combustible sensor in accordance with embodiments of the present invention. Sensor 30 includes holder 32 having catalyst 34 and reference 36 RTD elements. RTD elements 34 and 36 are thermally insulated from holder 32 by cement, Teflon, or a suitable high temperature epoxy as indicated at reference numeral 38. Holder 32 may be constructed from any suitable material that is able to support RTDs 34 and 36, but is preferably metal or a ceramic that is stable in the sensor application conditions. RTD elements 34 and 36 may be used in either the film or wire form, or any other suitable form and are preferably sealed in a protective cover 41, 43 that is preferably constructed of stainless steel. Thermal contact between RTD elements 34 and 36 and the RTD cover may be facilitated by using a thermoconductive material, such as a thermoconductive powder, cement, or epoxy as indicated at reference numeral 40. RTD elements 34 and 36 are sealed at a leading end with cement, or high temperature epoxy as indicated at reference numeral 42. The electrical leads coupling to RTDs 34 and 36 allow the variable physical signal corresponding to the temperature change of the device to be measured. A thin film of catalyst 44 is applied to the cover of catalyst RTD 34, while the cover of reference RTD 36 remains uncovered or protected by a ceramic film. Preferred catalysts include Group VIII noble metal catalysts, such as platinum, palladium, and rhodium and mixtures as well as metal oxide combustion catalysts. Other suitable catalysts include perovskite or hopcalite. Catalytic film 44 can also be made from solution, paste or powder and applied using thick or thin film techniques. The layer of the catalytic element is preferably relatively thin in order to promote conduction of the combustion heat to RTD element 34. The two RTD elements 34 and 36 are preferably placed in similar flow regions in the measured gas and have relatively close thermal mass, surface area and aerodynamic shape.

FIGS. 8-14 illustrate sensor sensitivity, accuracy, reproducibility, linearity, as well as stability in varying environments.

In summary, embodiments of the RTD-combustible sensor listed above preferably provide a functionally specific configuration of catalytic and reference elements having integral RTDs. The catalytic element has on its outside cover a catalytic film and relatively good thermal contact within a temperature measuring device. Both the catalytic RTD and the reference RTD are thermally isolated from each other and the catalyst is selected and merged with the RTD so that carbon monoxide, Co, (or other combustible species) are selectively oxidized to carbon dioxide, $CO_2$, on the catalyst surface. The catalyst and RTD cover should be in contiguous physical proximity and constructed to retain most of the heat of the combustion reaction on the catalyst film surface and adapted to transfer that heat to the RTD sensing element. The temperature of the catalyst RTD element is converted to an electrically measurable signal, i.e., voltage, current and is compared to the analogous signal from the reference RTD element. The signal difference is accordingly proportional to the combustible concentration in the measured gas mixture.

Sulfur Resistive Oxygen Sensor

Oxygen sensors and more particularly, potentiometric solid electrolyte oxygen sensors are known. Such sensors typically employ zirconia and are widely used in industrial applications for measuring excess oxygen partial pressure in various combustion processes. In one commercially available oxygen sensor, two porous platinum electrodes are deposited on opposite sides of a disc-shaped zirconia electrolyte. The response of the sensor to a differential in oxygen partial pressure on the reference (exposed to the gas mixture with known oxygen partial pressure, e.g., air) and the process side (exposed to the analyzed gas) obeys the Nernst type equation listed earlier in the Specification. As discussed above, the presence of platinum in a high sulfur environment leads to a degradation of the platinum electrode from the ceramic as well as rapid electrode deterioration. For the effective working electrode of the oxygen sensor, it is important that equally high electronic and ionic conductivities are provided in order to achieve a maximum of oxygen flux through the electrode. Mixed conducting oxides based on zirconia have been used in electrodes to improve the performance of electrochemical cells. For example, see U.S. Pat. No. 3,578,502, which discusses a stabilized zirconium oxide electrode for a solid electrolyte fuel cell. The structural and chemical integrity as well as the high thermal expansion coefficient (greater than $20 \times 10^{-6} K^{-1}$ are generally limiting factors for the application of acceptor-doped perovskite oxides $Ln_{1-x}A_xCO_{1-y}B_yO_{3-\delta A}$ (a=Ca, Sr, Ba; B=Fe, Cu, Ni, Mn) with very high electronic and significant ionic conductivity. These properties are discussed in the CRC Handbook of Solid State Electrochemistry by P. J. Gellings and H. J.-M. Bouwmeester (Eds.), CRC Press, Boca Roton-New York-London-Tokyo (1997) 615 pp.

In the past, sulfur tolerant composite electrodes based on oxides selected from the group of zirconium, yttrium, scandium, thorium, rare earth metals, and mixtures thereof were proposed. However, it is believed that more reliable mixed-conducting materials could be developed based on fluorite-type oxide ion conducting solid electrolytes, i.e. based on ceria, having considerably higher ionic and electronic conductivity. It is believed that electrodes based on these materials will be much more effective at having lower polarization resistivity. However, in the prior art, mixed conducting materials based on fluorite-type oxide ions have heretofore not been disclosed as being usable in sensors and particularly not in high sulfur resistive oxygen sensors, nor has information about the mixed conducting electrode and film properties with respect to such sensor been provided.

Figure 15:
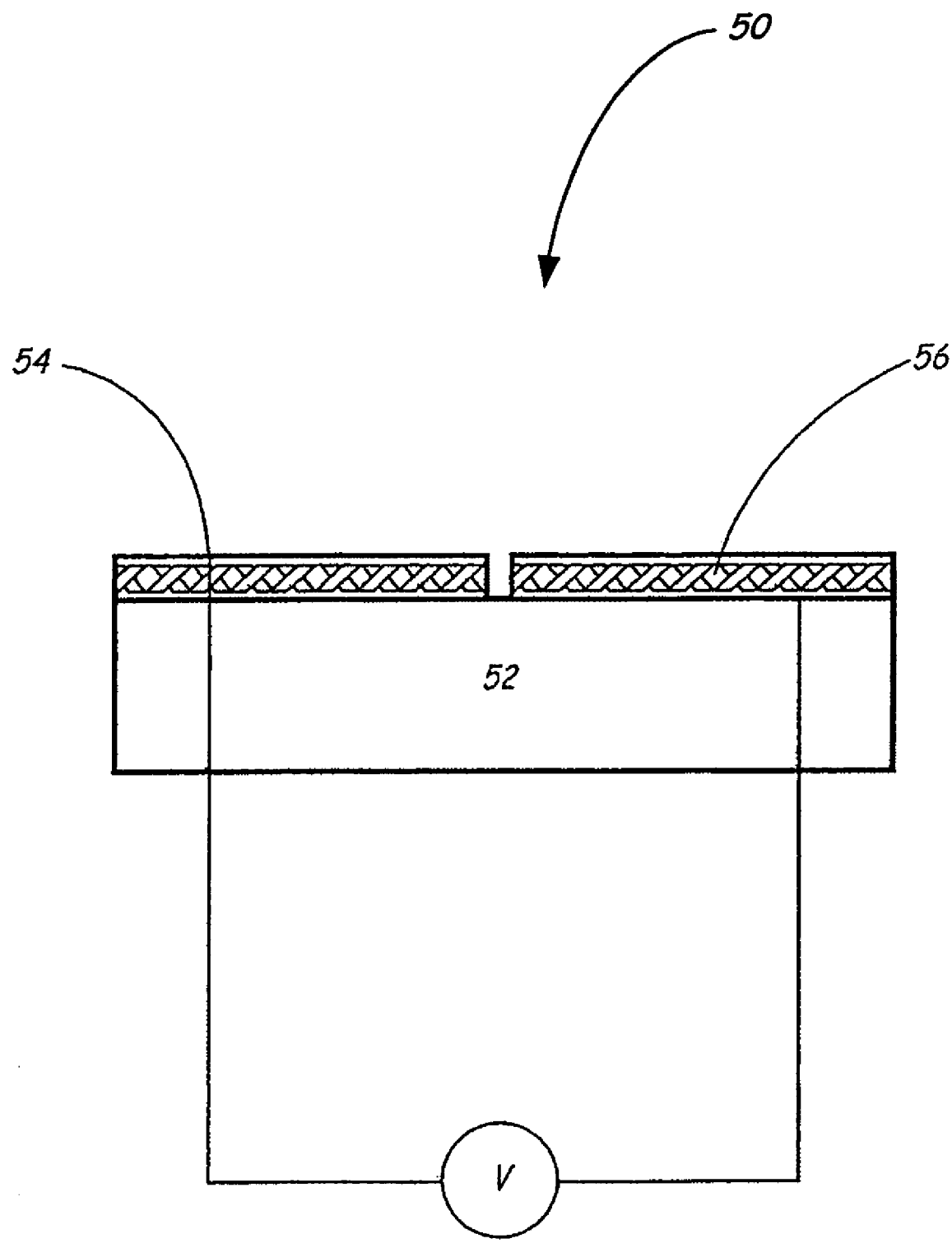
FIG. 15 is a diagrammatic view of a sulfur-resistant oxygen sensor in accordance with embodiment of the present invention.
Figure 16:
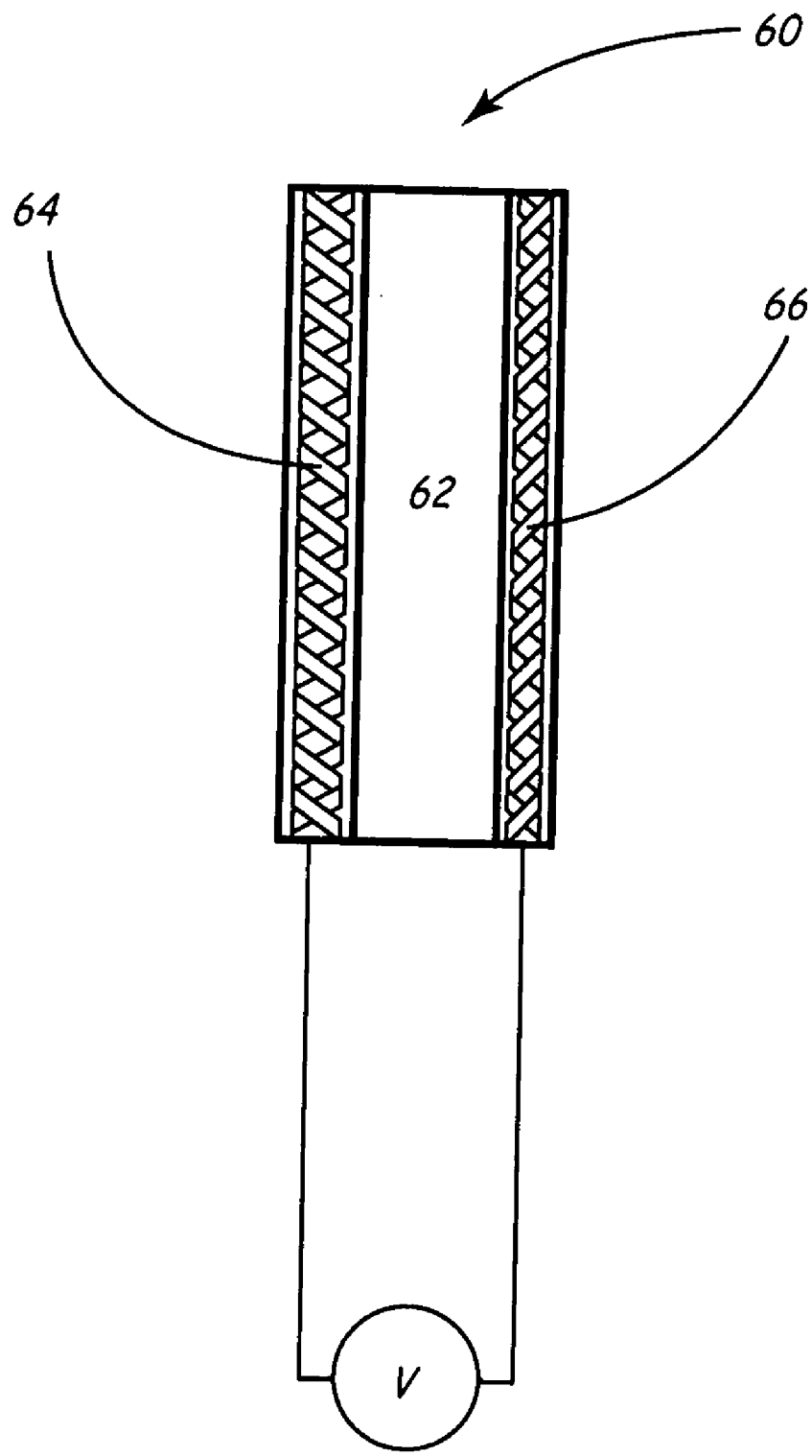
FIG. 16 is a diagrammatic view of a sulfur-resistant oxygen sensor in accordance with an alternate embodiment of the present invention.

In accordance with an embodiment of the present invention, an oxygen sensor consists of a solid electrolyte ceramic, consisting of mostly stabilized zirconia and two electrodes disposed thereon. The physical structure of the sensor is illustrated in FIGS. 15 and 16. FIG. 15 illustrates sensor 50 having a solid electrolyte ceramic 52 upon which are disposed reference electrode 54 and working/process electrode 56. Reference electrode 54 is exposed to a gas with a known partial pressure of oxygen, e.g., air and is preferably constructed from a metal chosen from the noble metal group (more preferably platinum). Process/working electrode 56 is exposed to the analyzed gas stream and is a mixed ionic/electronic conductor chosen from the ceria containing fluorite group of materials (preferably terbium or praseodymium stabilized ceria).

FIG. 16 is a diagrammatic view of an improved solid electrolyte oxygen sensor in accordance with an alternate embodiment of the present invention. Sensor 60 includes reference electrode 64 and working/process electrode 66 disposed on opposite sides of solid electrolyte 62. As with sensor 50, the working/process electrode 66 is preferably constructed using a mixed ionic/electronic conductor chosen from the ceria containing fluorite group of materials (preferably terbium or praseodymium stabilized ceria).

Figure 17:
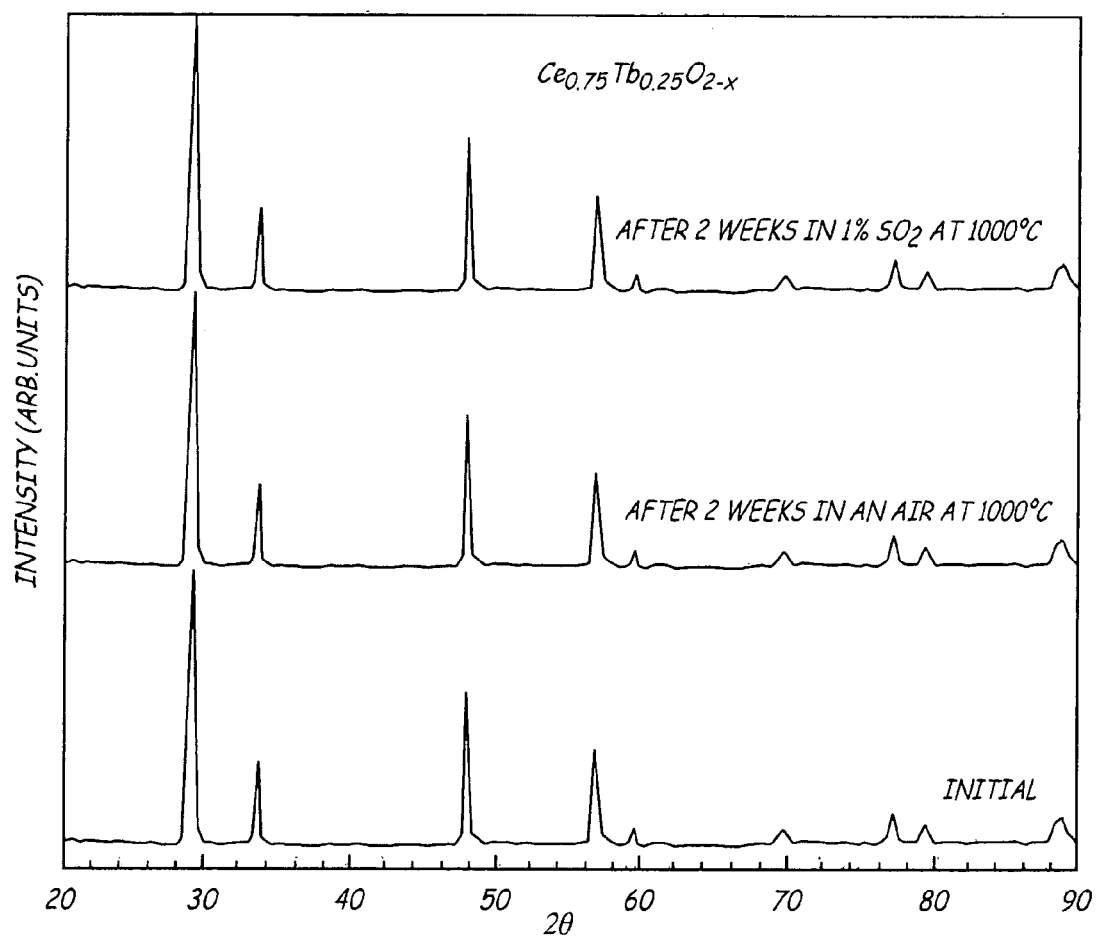
FIGS. 17, 18 and 19 illustrate sensor material stability in sulfur-containing atmosphere as evidenced from X-ray diffraction.

FIG. 17 illustrates X-ray diffraction measurements showing that there is no transformation of the fluorite structure nor phase separation of $CeO_2$, $TbO_{1.75}$ or sulfite/sulfide formation after two weeks of heat treatment at approximately 1,000° C. in the air or with exposure to sulfur dioxide ($SO_2$).

Figure 18:
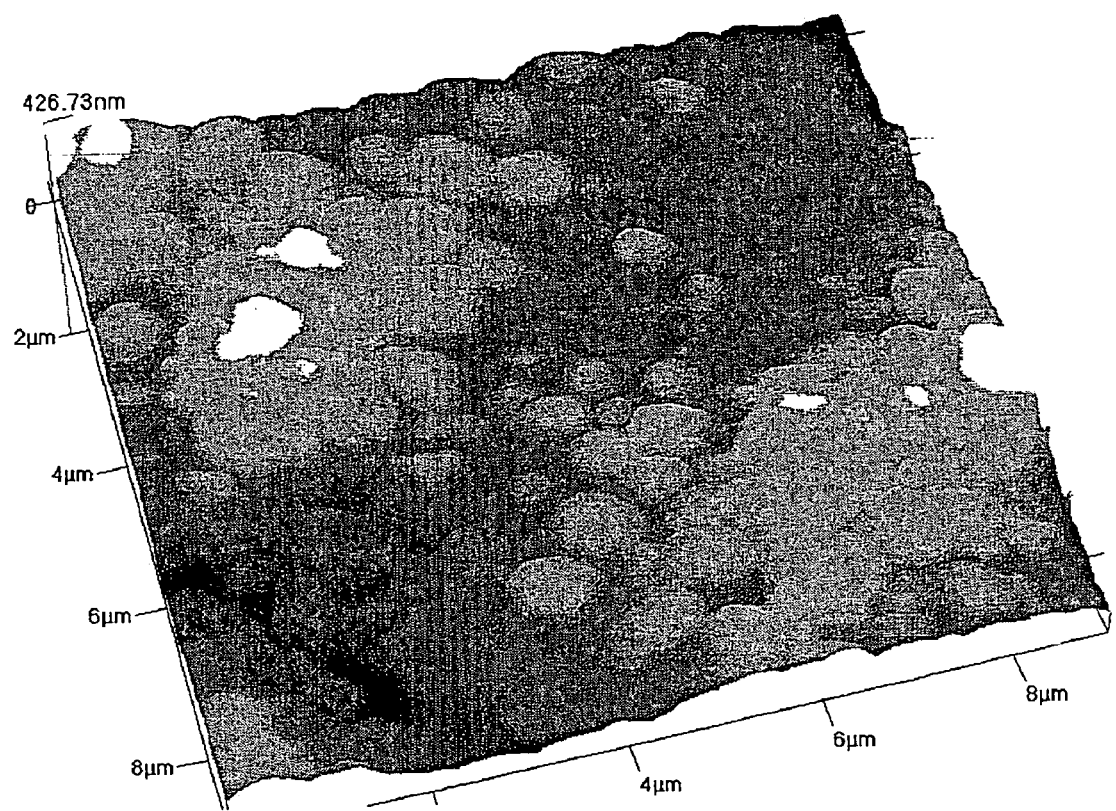

FIG. 18 is an atomic force microscope (AFM) topographical image of a $Ce_{0.80}Tb_{0.2}O_{1.90+\delta}$ film sample sintered at approximately 1,300° C. illustrating relatively small particles of uniform size, approximately 0.3-1 micrometer (μm) and very dense microstructure. As expected, these particles are considerably larger than those of the "as prepared" powder by the known hydrothermal method (approximately 20-50 nm).

Figure 19:
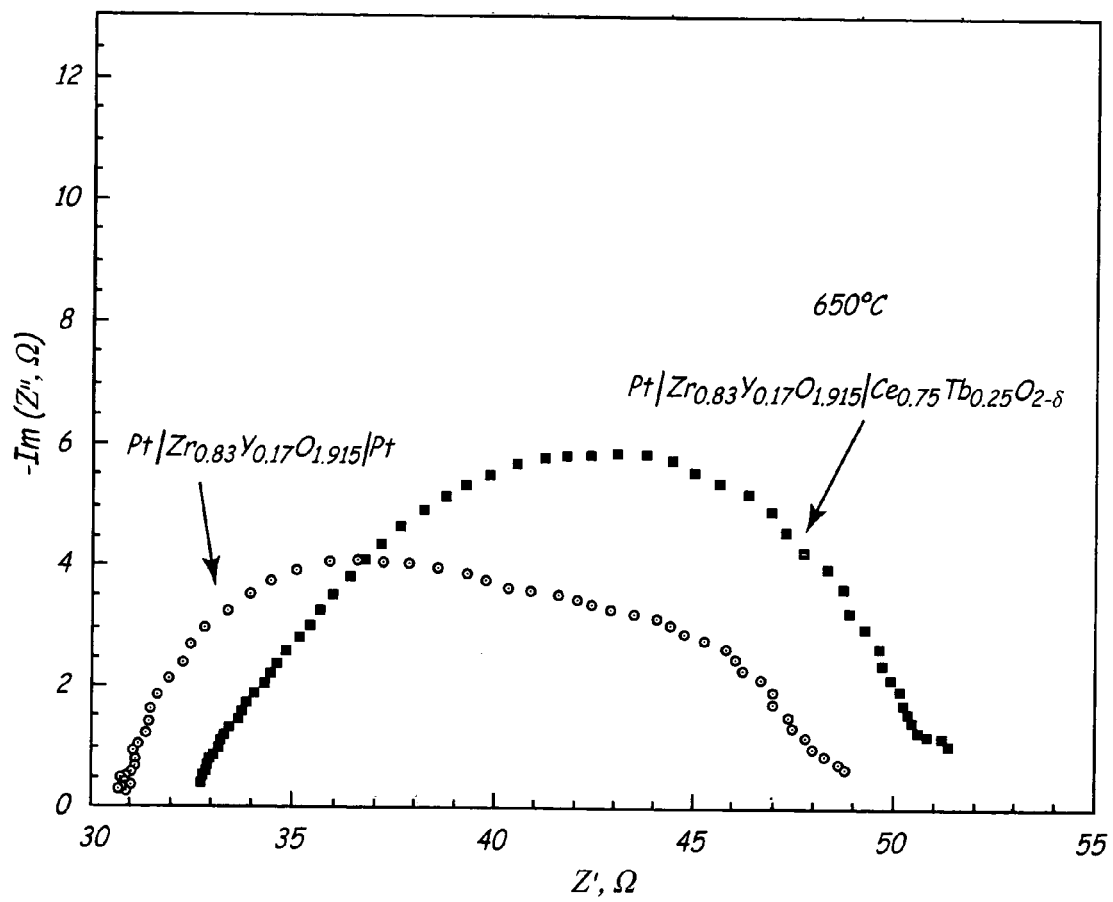

FIG. 19 is a diagrammatic chart illustrating impedance of an oxygen sensor with platinum electrodes and a mixed conductive working electrode.

Figure 20:
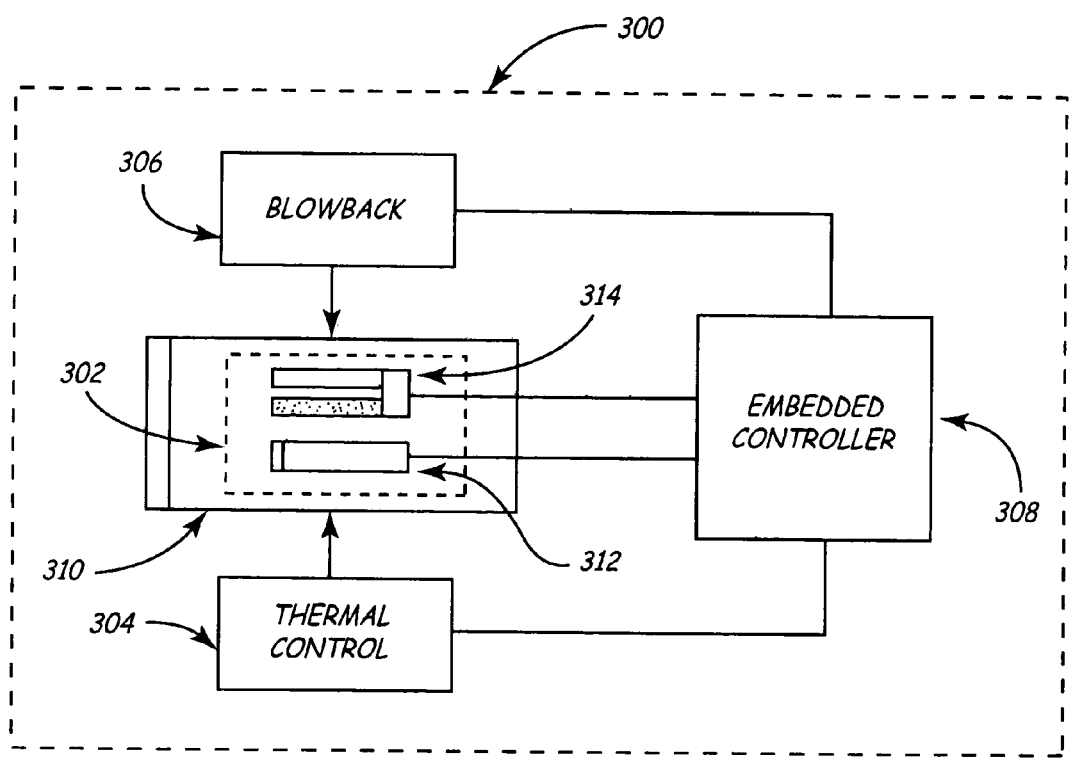
FIG. 20 is a diagrammatic view of a process analytic system in accordance with an embodiment of the present invention.

FIG. 20 is a diagrammatic view of a process analytic system in accordance with an embodiment of the present invention. System 300 includes improved sample probe 302 thermally coupled to thermal control system 304; electrically coupled to embedded controller 308; and fluidically coupled to blowback system 306. Probe 302 may contain any of the sulfur-resistant sensors described above, and preferably contains both an oxygen sensor and a combustibles sensor. Probe 302 is preferable constructed within a particulate filtered enclosure such as those available from Mott Corp. of Connecticut. Within enclosure 310, the preferably multiple sensor element 312, 314 are preferably disposed on a plurality of concentric cylindrical members. Each of sensors 312, 314 is coupled to embedded controller 308, which is preferably an embedded PC controller such as the PC/104 Standard Controller.

Probe 302 is also coupled to thermal control system 304 to maintain probe 302 at a desired temperature. While system 304 is illustrated external to probe 302, it may be disposed within or integral with probe 302. Thermal control system 304 includes a heating element (not shown) and a temperature sensor (not shown in FIG. 20) that is used to provide an indication of probe temperature. Since some embodiments of the sensors described herein include thermally sensitive elements, it is contemplated that the temperature sensing function of thermal control module 304 can be performed with temperature sensor already present within probe 302.

Blowback system 306 is fluidically coupled to probe 310 and is used to periodically reverse gas flow through the probe to thereby dislodge any built-up particulate matter on probe 302. Preferably blowback system 306 includes its own thermal control system, or other means of controlling the blowback gas temperature such that blowback gas is temperature-matched to the probe temperature to minimize thermal shock to probe 302 during blowback.

The system illustrated in FIG. 20 provides high level system functions in a robust manner and can withstand sulfur-containing environments effectively. The high level functions of embedded controller 308 and the fact that it is coupled to probe 302, thermal control module 304 and blowback system 306, allow the system to be easily calibrated for zero and span. Further, the advanced processing abilities of controller 308 facilitate the provision of diagnostics that may potentially identify probe deterioration or failure more effectively.

Although the present invention has been described with reference to preferred embodiments, workers skilled in the art will recognize that changes may be made in form and detail without departing from the spirit and scope of the invention. For example, intermediate materials can be used in the construction of the structures disclosed herein to enhanced the compatibility of the material's coefficients of thermal expansion, thereby reducing the possibility of thermally induced stresses and potential cracking/fractures.

What is claimed is:

1. A solid state device for determining the concentration of oxygen in a gas phase,
   the solid state device comprising:
   a solid electrolyte;
   a reference electrode coupled to a surface of the solid electrolyte and being exposed to a gas with a known partial pressure of oxygen; and
   a working electrode including a mixed ion/electron conductor constructed from a ceria solid solution doped with at least one mixed valency element, wherein the working electrode is coupled to the same surface of the solid electrolyte as the reference electrode.

2. The device of claim 1 wherein the solid electrolyte is selected from the group consisting of doped zirconia and ceria.

3. The device of claim 1 wherein the reference electrode is constructed from a metal oxide electrode.

4. The device of claim 3 wherein the metal oxide electrode includes perovskite structure.

5. The device of claim 3 wherein the metal oxide electrode includes oxide with fluorite structure.

6. The device of claim 1 wherein the mixed valency element is one of terbium and praseodymium.

* * * * *

UNITED STATES PATENT AND TRADEMARK OFFICE
CERTIFICATE OF CORRECTION

PATENT NO. : 7,527,717 B2  Page 1 of 1
APPLICATION NO. : 10/607856
DATED : May 5, 2009
INVENTOR(S) : Shuk et al.

It is certified that error appears in the above-identified patent and that said Letters Patent is hereby corrected as shown below:

On the title page item (56),
Under References Cited, Other Publications, insert the reference --T. Takahashi (Ed.), High Conductivity Solid Ionic Conductors, World Scientific, Singapore (1989).--

Signed and Sealed this

Twenty-ninth Day of September, 2009

David J. Kappos
*Director of the United States Patent and Trademark Office*